United States Patent [19]

Moran et al.

[11] Patent Number: 4,874,385
[45] Date of Patent: Oct. 17, 1989

[54] PLUNGER LOCK DEVICE

[75] Inventors: John P. Moran, Herculaneum; Richard W. Gilson, Dellwood; Thomas W. Heubel, Chesterfield, all of Mo.

[73] Assignee: Sherwood Medical Company, St. Louis, Mo.

[21] Appl. No.: 133,302

[22] Filed: Dec. 16, 1987

[51] Int. Cl.$^4$ .............................................. A61M 5/00
[52] U.S. Cl. .................................... 604/208; 604/210
[58] Field of Search ............... 604/218, 220, 228, 207, 604/208, 210, 211

[56] References Cited

U.S. PATENT DOCUMENTS

| | | |
|---|---|---|
| 1,644,901 | 10/1927 | Stieglitz . |
| 1,703,427 | 2/1929 | Langbein . |
| 1,798,116 | 3/1931 | Brockway . |
| 1,863,785 | 6/1932 | Dickinson . |
| 2,002,024 | 5/1935 | Wood . |
| 2,216,354 | 10/1940 | Pletcher . |
| 2,221,739 | 11/1940 | Reiter . |
| 2,474,496 | 6/1949 | Rayman . |
| 2,856,925 | 10/1958 | Helmer et al. . |
| 2,869,541 | 1/1959 | Helmer et al. . |
| 3,563,240 | 2/1971 | Silver . |
| 3,730,389 | 5/1973 | Harris et al. .......................... 222/31 |
| 3,831,602 | 8/1974 | Broadwin . |
| 4,153,056 | 5/1979 | Silver et al. . |
| 4,246,898 | 1/1981 | Travalent et al. . |
| 4,275,729 | 6/1981 | Silver . |
| 4,444,335 | 4/1984 | Wood et al. ............................ 222/43 |
| 4,546,859 | 10/1985 | Newman ................................ 188/67 |
| 4,562,844 | 1/1986 | Carpenter et al. ............... 604/228 X |
| 4,610,672 | 6/1985 | Ewalt et al. ........................... 604/220 |
| 4,642,102 | 2/1987 | Ohmori ................................. 604/210 |
| 4,715,854 | 12/1987 | Vaillancourt ........................ 604/191 |

FOREIGN PATENT DOCUMENTS 1577954 7/1969 France .............................. 604/210

Primary Examiner—John D. Yasko
Attorney, Agent, or Firm—Stanley N. Garber; Andrew J. Beck; William R. O'Meara

[57] ABSTRACT

The present invention resides in an improvement to a syringe having a syringe housing and a plunger slidably positioned therein and extendable therefrom, and includes a novel locking member mounted on the plunger externally of the housing and angularly movable thereon between a first position in which the locking member can move longitudinally along the plunger and a second position in which the locking member becomes engaged with the plunger to hold the members together in fixed condition for movement in concert. The locking member is also shaped to move into abutment with the syringe housing where the plunger is moved to limit movement of the plunger when in its locked position.

13 Claims, 1 Drawing Sheet

PLUNGER LOCK DEVICE

The present invention relates to means to control and/or preset the possible travel of a syringe plunger in order to control the amount of substance contained in the syringe that can be dispensed by operation of the plunger moving therein. The present device includes a locking member mounted on the plunger portion of the syringe externally of the syringe housing and in position to move against the rear end wall of the syringe housing as the plunger is advanced in the housing during a dispensing operation to limit movement thereof. The invention resides primarily in the locking member which in the form shown is an annular member mounted on the plunger portion such as on a winged plunger portion of a type used on many syringes. The locking member has two operative positions on the plunger portion including a first position wherein the locking device is free to move longitudinally along the plunger portion and a second position angularly related to the first position wherein cam means on the locking member engage the plunger portion to lock the locking member in position thereon. In the locked position the locking member moves in concert with the plunger and controls the amount of possible plunger movement into the syringe housing and hence limits the amount of substance that can be dispensed therefrom. This amount can be easily changed by relocating the locking member on the plunger portion.

Various known plunger locking devices are disclosed and described in the prior art. One of the more pertinent prior art patents in this regard is Ewalt et al U.S. Pat. No. 4,610,672 which is assigned to Applicants' assignee. The locking means disclosed in the Ewalt et al patent is fixed to the rear end of the syringe housing, and to lock the plunger member in position the plunger is rotated in the housing and is locked in position and in this position the plunger member is not able to be moved to dispense substance therefrom. The construction disclosed in the Ewalt et al patent cannot be used to control and/or preset the amount of dosage to be expelled from a syringe as in the present device, but instead, it is used to lock the plunger on the syringe at some desired fixed position.

Wood et al U.S. Pat. No. 4,444,335 discloses means to regulate the amount of material that can be expelled from a syringe and includes a stop member positionally adjustable along a plunger rod and engageable with the plunger rod by engagement with a selected one of a plurality of spaced grooves formed along one side of the plunger rod. With the Wood et al construction, when it is desired to adjust the position of the stop member on the plunger rod, and thus the distance the plunger can move in the syringe, the stop member is moved longitudinally from a position engageable with one plunger groove to a position engageable with another groove. Therefore the number of dosage possibilities with the Wood et al construction is limited to the width and spacing of the grooves formed in the side of the plunger rod while with the present device any dosage size within the limits of the syringe portion are possible. The Wood et al device also requires complicated multi part locking means unlike anything included in the present device.

Helmer et al U.S. Pat. No. 2,856,925 shows another form of a plunger lock and the present construction differs from the construction disclosed therein for many of the same reasons that distinguish it from the Wood et al construction.

There are other known constructions which have lock members on plunger rods including some that are threaded onto a syringe plunger rod to act as a stop member to control movement of the plunger. See for example, Travalent et al U.S. Pat. No. 4,246,896. In the Travalent et al construction the stop member is not held in position securely and can be moved relatively easily, even accidentally, to alter the position thereof and to change the dosage.

Other known patents which show various plunger locking devices are disclosed in the following listed U.S. Pat. Nos.: Stieglitz U.S. Pat. No. 1,644,901; Langbein U.S. Pat. No. 1,703,427; Brockway U.S. Pat. No. 1,798,116; Dickinson U.S. Pat. No. 1,863,785; Wood U.S. Pat. No. 2,002,024; Pletcher U.S. Pat. No. 2,216,354; Reiter U.S. Pat. No. 2,221,739;Rayman U.S. Pat. No. 2,474,496; Silverstein U.S. Pat. No. 2,479,645; Helmer et al U.S. Pat. No. 2,856,925; Helmer et al U.S. Pat. No. 2,869,541; Helmer et al U.S. Pat. No. 2,875,761; Silver U.S. Pat. No. 3,563,240; Harris, Sr. et al U.S. Pat. No. 3,730,389; Broadwin U.S. Pat. No. 3,831,602; Silver et al U.S. Pat. No. 4,153,056; Silver et al U.S. Pat. No. 4,275,729; Newman U.S. Pat. No. 4,546,859 and Ohmori U.S. Pat. No. 4,642,102.

THE PRESENT INVENTION

The present invention is directed to a novel, relatively simple inexpensive plunger locking device which is easy to operate and locks onto a syringe plunger portion for movement therewith as distinguished from being part of the syringe housing. The present locking device can be locked into any desired position along the length of the plunger portion, and is positioned on the plunger portion so as to engage the end wall of the syringe housing to control and limit movement of the plunger in one direction, and hence to control the amount of dosage dispensed from the syringe for any one operation thereof. It is important to the present invention that the locking device be able to be preset to any desired position along the plunger portion to determine and control dosage, and thus the present device overcomes many of the disadvantages and shortcomings associated with the known prior art. The present plunger stop includes a twist to lock member mounted on the plunger and designed so that in one position thereof it is slidable along the plunger portion to any desired position and is movable to a second position on the plunger portion angularly related to the first position whereby it engages the plunger portion, or the winged portions thereof, when used, and locks the lock member in position on the plunger portion. In this position the plunger and the lock member move in concert. The subject lock member is shown as being of annular construction and as having at least one, and preferably two, circumferentially beveled cam portions preferably arranged in opposed relation to engage opposed portions of the plunger portion member. More particularly, the cam portions engage with a pair of opposed winged portions of the plunger portion in a locked position by positively engaging and preferably biting or cutting into the wing portions to form grooves therein while also establishing a tight fitting connection therewith. When two opposed cam portions are used, their lengths in the circumferential direction should be less than the distance between adjacent wing portions which form the plunger portion so that the lock member is free to move along the plunger portion in the unlocked position. The cam or cams preferably have relatively sharp edges, and the lock member including the cams is preferably formed of a harder material than the plunger portion so that the cam will dig into and may actually cut grooves in the plunger portion or enter previously cut grooves if desired. Thus, the present locking device can be locked in any desired position along the plunger portion and can be loosened so that it can be moved from one position to another relatively easily. Furthermore, the lock member can include stops adjacent to the cams to limit movement thereof into engagement with the plunger portion, and when locked the locking member cannot be easily dislodged either accidentally or unintentionally because of the tight fitting connection between the locking member and the plunger portion. The locking member also preferably has opposed outwardly extending tabs or handles formed thereon to facilitate gripping the locking member to move or rotate it between its locked and unlocked positions.

It is therefore a principal object of the present invention to provide novel means for controlling and presetting the travel of a plunger and connected piston portion of a syringe.

Another object is to provide means that can be locked onto a syringe plunger portion at any desired position along the length thereof and in position to engage a surface of the syringe housing to thereby control the amount of dosage that can be dispensed by controlling the amount of possible movement of the plunger.

Another object is to provide a member for locking onto a syringe plunger portion for movement therewith.

Another object is to provide relatively simple, inexpensive and easy to operate means for adjusting and controlling the amount of dosage that can be expelled from a syringe.

Another object is to precisely predeterminately set the travel of a syringe plunger.

Another object is to provide means to facilitate changing the dosage of substance that can be dispensed from a syringe.

Another object is to modify existing syringes to enable better control over the amount of dosage that can be dispensed therefrom.

Another object is to make it possible for a doctor or a nurse to select the size dosage to be administered by syringe.

Another object is to provide a plunger lock means which can be locked onto and move with a syringe plunger portion.

These and other objects and advantages of the present invention will become apparent to those skilled in the art after considering the following detailed specification which discloses a preferred embodiment of the subject device in conjunction with the accompanying drawing which forms a part thereof, and wherein:

DETAILED DESCRIPTION OF PREFERRED EMBODIMENT

Figure 1:
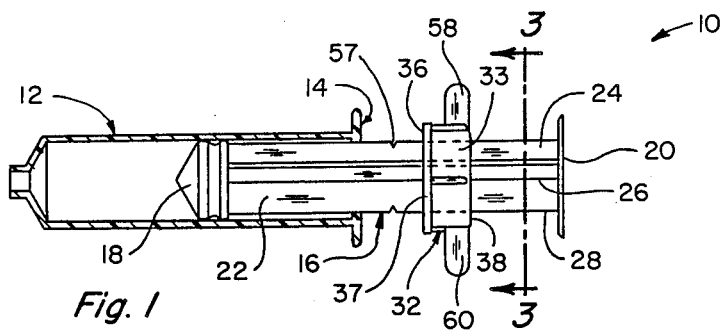
FIG. 1 is a cross-sectional elevational view of a syringe having lock means mounted on the plunger portion constructed according to the present invention, said sYringe being shown with its plunger in a withdrawn condition.
Figure 2:
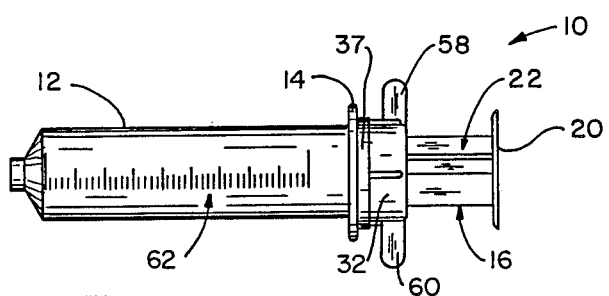
FIG. 2 is a side elevational view of the syringe shown in FIG. 1 with its plunger shown in its retracted position and under control of the setting of the lock means.

Referring to the drawing more particularly by reference numbers, number 10 in FIGS. 1 and 2 identifies a syringe constructed according to the teachings of the present invention. The syringe includes a syringe housing or barrel 12 with an end wall portion 14 on the rear end thereof. The syringe has a syringe plunger assembly 16 with a piston portion 18 on one end located inside the syringe housing 12 and an operator portion 20 on the opposite end thereof outside of the housing. The portion 20 is the portion that is pushed by the operator when expelling substance from the syringe. The plunger assembly 16 also includes a rod or plunger portion 22 which extends between and connects the piston portion 18 with the operator portion 20. The plunger portion 22 may have several different cross-sectional shapes including being formed by a plurality of wing portions including pairs of opposed radial wings 24 and 26, and 28 and 30.

Of special interest to the present invention is lock member 32 which is shown positioned on the plunger portion 22 in the location between the rear wall 14 of the syringe housing 12 and the plunger operator end 20.

Figure 3:
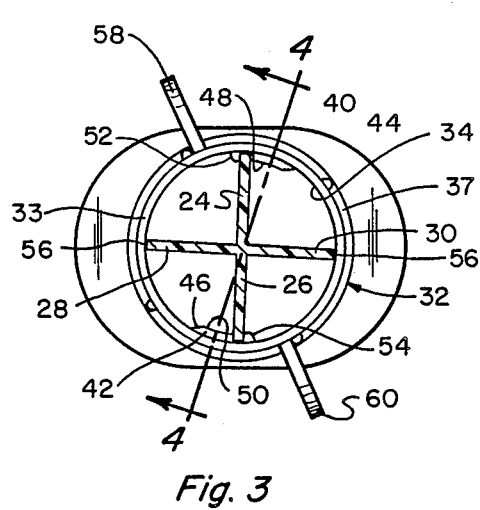
FIG. 3 is a cross-sectional view taken on line 3—3 of FIG. 1.
Figure 4:
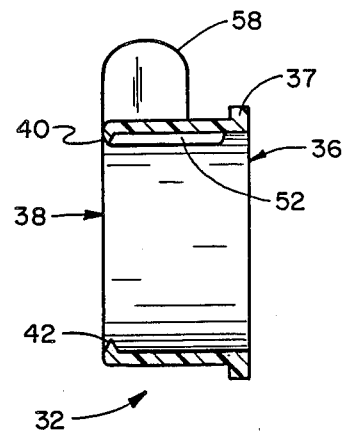
FIG. 4 is a cross-sectional view taken along line 4—4 of FIG. 3.

The locked member 32, as best shown in FIG. 3, has an annular portion 33 with an opening 34 formed therethrough which is sized to slidably receive the plunger portion 22 so that in its unlocked condition it will be able to move longitudinally along the plunger portion 22 to relocate it at any position therealong within the range thereof. This is important because it means that the user can adjust the position of the lock member 32 to any desired position to precisely control the amount of substance that can be dispensed from the syringe 10 and hence to accurately control the dosage that is given to a patient or for some other purpose.

The lock member 32 also has a second or locked position on the plunger portion 22 wherein the lock member 32 and the plunger member 16 are so engaged with each other that they must move in concert. In the construction shown in FIGS. 1 and 3 the outer edges of the wing portions 24–30 define 4 points on a circle, which circle approximates the diameter of the opening 34 through the lock member 32. It is possible, and contemplated however to construct the cross-sectional shape of the plunger portion 22 and of the opening 34 through lock member 32 to be different from a circle and still apply the teachings of the present invention. However, for simplicity of explanation the circular shape of for the opening 34 and the winged shape the plunger portion 22 are shown to illustrate the teachings of the present invention. Furthermore, as shown in FIG. 1, the locking member 32 has spaced opposite ends 36 and 38 with the end 36 at the forward end of the lock member 32 being somewhat larger in diameter (or having an outwardly extending projection 37) which extend far enough so that the projecting portion 37 will bump against the rear end wall 14 of the syringe housing 10 to limit movement of the plunger member during a dispensing operation.

Referring to FIG. 3 the surface of the opening 34 through the lock member 32, at a suitable location such as adjacent the rear end wall 38, has one or more inwardly extending cam portions 40 and 42, two being shown, which are shaped to have leading beveled cutting edges 44 and 46 respectively and elongated arcuate shaped edge portions 48 and 50. Each of the cams 40 and 42 also has a radial inwardly extending portion 52 and 54 adjacent corresponding ends thereof so that when the lock member 32 is turned or rotated on the plunger portion 22 the cutting edges 44 and 46 and thereafter the arcuate edge portions 48 and 50 will engage and cut or form grooves in the free edges, such as free edges 56 of the plunger wings 24–30 in FIGS. 1, 2 and 3. As the twisting of the locking member on the plunger portion 22 is continued, the cam surfaces 48 and 50 will move in the grooves, such as grooves 57 (FIG. 1), until the free edges 56 of the respective wings move into engagement with the inwardly extending portions 52 and 54 which form stops to limit the relative angular movement between the members. Twist grips 58, 60 are formed on the lock member 32 to facilitate twisting the lock member 32 on the plunger portion 22. In this position which is the locked position, the lock member 32 will be securely attached to the plunger 16 and the two members will thereafter move in concert with each other until the lock member 32 is again rotated in the opposite direction on the plunger portion 22 to free the locking member therefrom so that it can again be moved longitudinally along the plunger portion 22 to relocate it for establishing a different dosage.

The lock member 32 is preferably constructed of a harder material such as a harder plastic material than is used in the construction of the plunger portion 16, which may also be formed of plastic. This is done so that when the lock member is moved from its unlocked condition to its locked condition, the cam portions 40 and 42 will not only tightly engage the edges 56 of the respective plunger wings 24–30 but the cam portions should preferably also be sharp enough to cut groove in the wing portions which grooves will remain even after the lock member has been moved to its unlocked condition. This is an advantage because it means that previously formed grooves can be used to relocate the locking member on the plunger portion at the same location at a later date if it is desired to repeat the same dosage. It also means that the locking member can be used to establish any desired dosage within the range thereof. No known syringe device has these desirable characteristics. It also means that once a desired dosage has been established it can be maintained indefinitely because of the tight interference fit between the lock member and the plunger. There may also be situations where the same plunger can be used with several different syringe housings and wherein it may be desired to use the same or a different dosage. This is possible with the present construction.

It is also contemplated to construct a plunger portion having different cross-sectional sizes and shapes so long as sufficient clearance is provided to enable the locking member to move longitudinally relative thereto in one position and when rotated to cut grooves and maintain a tight fitting connection between the locking member and the plunger in the locked position. Another cross-sectional shape for the plunger portion that is suitable is a plunger portion having a triangular shaped cross-section. In such case an annular locking member such as described herein with one, two or three spaced cam portions could be used to engage the apexes of the triangular shaped plunger as aforesaid.

It is also contemplated to provide a graduated scale 62 extending along the surface of the syringe housing 12 so that the user can determine visually from the scale how far the plunger needs to move to dispense a desired dosage. With the present device the dosage can be preset when the syringe is empty or full and the present syringe construction permits the user to have one hand free while expelling a dosage thereby enabling the other hand to be used for other purposes such as to hold the person's arm or flesh while administering an injection. Having the dosage preset in this manner illustrates that the user can depress the plunger until it has stopped, at which time he knows that the correct dosage has been ejected. He can thereafter reposition the locking member, apply another needle, and use the same syringe to administer a second or third injection from the same or different needles. Use of the present syringe may also mean that the needle need be in the patient for a shorter period of time than otherwise since the doctor or nurse does not need to visually determine when to stop moving the plunger while dispensing the dosage.

Thus, there has been shown and described novel means for controlling and/or presetting the travel of the syringe plunger or like device, which means fulfill all the objects and advantages sought therefor. It will be apparent to those skilled in the art, however, that many changes, modifications, variations and other uses and applications for the subject device are possible and contemplated, and all such changes, modifications, variations and other uses and applications which do not depart from the spirit and scope of the invention are deemed to be covered by the invention which is limited only by the claims which follow.

What is claimed is:

1. In a syringe having a syringe housing with a plunger slidably positioned therein and extendable therefrom, the improvement comprising a locking member mounted on the plunger externally of the syringe housing, said locking member and said plunger having means cooperatively engageable in selected relative positions thereof including inwardly extending cam means on the locking member and means on the plunger member engageable therewith in said selected relative position, said locking member being angularly movable on the plunger between a first position in which the locking member is free to be moved along the length of the plunger to any desired position therealong and a second position angularly related to the first position in any desired position therealong whereby said cooperatively engageable means become engaged so that the locking member and the plunger move in concert, said last named second position limiting longitudinal movement of the plunger relative to the syringe housing.

2. In the syringe of claim 1 wherein the plunger includes a plurality of elongated radially extending wing portions extending outwardly from a central location to respective free edges, said locking member being annular and said cooperatively engageable means include at least one inwardly extending portion which when the locking member is moved angularly on the plunger the inwardly extending portion engages the free edge of one of the plunger wings in the second position thereof.

3. In the syringe of claim 2 said locking member has a pair of spaced inwardly extending portions positioned to simultaneously engage the free edges of respective plunger wing portions when the locking member is moved angularly from its first to its second position.

4. In the syringe of claim 2 said locking member includes means to limit angular movement thereof toward the second position.

5. In the syringe of claim 1 wherein the syringe housing has an end wall with an opening therethrough through which the plunger extends and can move, said locking member on the plunger limiting movement of the plunger in one direction through the opening when in its second position.

6. In the syringe of claim 2 wherein the locking member includes at least one outwardly extending portion positioned to facilitate gripping and movement thereof on the plunger.

7. In the syringe of claim 2 wherein the annular locking member has opposite ends, one of which engages the syringe housing to limit movement of the plunger in one direction, the inwardly extending portion being located on the locking member adjacent to the other opposite end thereof.

8. In the syringe of claim 1 wherein the locking member is formed of a harder material than the plunger.

9. In the syringe of claim 2 wherein the annular locking member is formed of a harder material than the plunger and the inwardly extending portions thereof have relatively sharp inwardly facing edges for engaging the plunger.

10. In the syringe of claim 2 wherein the inwardly extending portions are elongated circumferentially and have a circumferentially beveled portion.

11. A locking member for positioning on the plunger portion of a syringe externally of the syringe housing comprising a member having an opening therethrough that is shaped to receive the plunger portion and to be able to move therealong, said locking member being angularly movable on said plunger portion and having means thereon cooperatively engageable with the plunger portion by cutting a groove in the plunger portion during relative angular movement therebetween to lock the locking member onto the plunger portion for movement in concert therewith.

12. The locking member of claim 11 wherein the plunger portion includes a plurality of elongated radially extending wing portions each having an outer free edge along one side thereof, said cooperatively engageable means on the locking member having at least one inwardly extending portion engageable with the free edge of one of the wing portions when said member is moved to a preselected angular position on the plunger portion.

13. The locking member of claim 12 wherein the locking member has at least two circumferentially spaced inwardly extending means positioned to simultaneously engage the free edges of respective wing portions of the plunger.

* * * * *